United States Patent
Bauss et al.

(10) Patent No.: US 6,476,008 B1
(45) Date of Patent: Nov. 5, 2002

(54) USE OF DIPHOSPHONIC ACIDS OR THE PHYSIOLOGICALLY ACCEPTABLE SALTS OR ESTERS THEREOF IN THE PREVENTIVE TREATMENT OF AFTER-EFFECTS RESULTING FROM ENLARGEMENT OR REPLACEMENT OF THE BLADDER

(75) Inventors: Frieder Bauss, Neuhofen; Drasko Brkovic, Leimen, both of (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 09/423,485

(22) PCT Filed: May 8, 1998

(86) PCT No.: PCT/EP98/02712

§ 371 (c)(1),
(2), (4) Date: Dec. 27, 1999

(87) PCT Pub. No.: WO98/51314

PCT Pub. Date: Nov. 19, 1998

(30) Foreign Application Priority Data

May 9, 1997 (DE) .......................................... 197 19 680

(51) Int. Cl.[7] .............................................. A61K 31/66
(52) U.S. Cl. ....................................................... 514/108
(58) Field of Search ................................ 514/102, 104, 514/106, 108

(56) References Cited

U.S. PATENT DOCUMENTS

| | | |
|---|---|---|
| 4,624,947 A | 11/1986 | Blum et al. |
| 4,711,880 A | 12/1987 | Stahl et al. |
| 4,927,814 A | 5/1990 | Gall et al. |
| 4,939,130 A | 7/1990 | Jaeggi et al. |
| 4,980,171 A | 12/1990 | Fels et al. |
| 5,358,941 A | 10/1994 | Bechard et al. |
| 5,599,291 A * | 2/1997 | Balbierz et al. ............... 604/8 |
| 5,681,590 A | 10/1997 | Bechard et al. |
| 5,882,656 A | 3/1999 | Bechard et al. |

FOREIGN PATENT DOCUMENTS

| | | |
|---|---|---|
| EP | 0 275 468 | 7/1988 |
| EP | 0 531 253 | 3/1993 |
| EP | 0 566 535 | 10/1993 |
| EP | 0 625 355 | 11/1994 |
| WO | WO 93/09785 | 5/1993 |
| WO | WO 93/21907 | 11/1993 |
| WO | WO 94/12200 | 6/1994 |
| WO | WO 94/14455 | 7/1994 |
| WO | WO 95/29679 | 11/1995 |
| WO | WO 96/19998 | 7/1996 |
| WO | WO 96/35407 | 11/1996 |

OTHER PUBLICATIONS

Russell et al., "Experimental renal osteodystrophy . . . ", Journal of Clinical Investigation, 1975, vol. 56/3, pp. 548–554.*
Trechsel et al., Relation between bone mineralization, calcemia and intestinal . . . , Vitam. D probl. relat. Uremic bone dis., proc. Workshop, 2nd., 1975, pp. 91–95.*
Wojtowcz et al., "Effect of biphosphates on the process of biological mineralization . . . " Polski tyfodnik lekarski(poland), Nov. 1995, vol. 50 pp. 45–47.*
English Abstract for Document B1, EP 625 355, Nov. 23, 1994.
English Abstract for Document B2, EP 275 468, Jul. 27, 1988.
English Abstract for Document B6, EP 566535, Oct. 20, 1993.
Mundy, et al, Calcium Balance, Growth and Skeletal Mineralisation in Patients with Cystoplasties, British Journal of Urology, vol. 69, pp. 257–259 (1992).
Wagstaff, et al., Delayed linear growth in Children with entercystoplasties, British Journal of Urology, vol. 69, pp. 314–317 (1992).
Database WPI , Week 9608, Derwent publication Ltd., London GB AN 96–074761 XP002076298 & JP 07 330 613A.

* cited by examiner

Primary Examiner—William R. A. Jarvis
Assistant Examiner—Vickie Kim
(74) Attorney, Agent, or Firm—George W. Johnston; Patricia S. Rocha-Tramaloni

(57) ABSTRACT

The invention relates to use of diphosphonic acids or physiologically compatible salts or esters thereof for preventive treatment of disturbances to ossary mineralization which may occur after operative extension of the urine bladder by augmentation plasties or replacement of the urine bladder by replacement plasties but often do not appear until years after the operation.

6 Claims, No Drawings

USE OF DIPHOSPHONIC ACIDS OR THE PHYSIOLOGICALLY ACCEPTABLE SALTS OR ESTERS THEREOF IN THE PREVENTIVE TREATMENT OF AFTER-EFFECTS RESULTING FROM ENLARGEMENT OR REPLACEMENT OF THE BLADDER

BACKGROUND OF THE INVENTION

The invention relates to the use of diphosphonic acids or physiologically compatible salts or esters thereof for preventive treatment of after-effects which may occur after operative extension of the urine bladder by augmentation plasties or replacement of the urine bladder by replacement plasties but often do not appear until years after the operation.

For various reasons it may be necessary to dilate the urine bladder (bladder augmentation plasty) or even to replace it (bladder replacement plasty). At present this surgical intervention is generally performed with various segments of the intestine or stomach tissue as extension or replacement plasties.

The most frequent indication for extension plasty in childhood and youth relates to patients with functional disorders in emptying the bladder (Spina bifida, children with open or closed fissuration), who often have kidney insufficiency of varying severity in addition to the disorder in emptying the bladder. Recent investigations show that children with inserts of intestine in the urine bladder or with complete replacement of the urine bladder by intestine have their growth in height significantly reduced by 20 to 50% (cf. A. R. Mundy, D. E. Nurse: Calcium balance, growth and skeletal mineralisation in patients with cystoplasties. Br. J. Urol. 69; 257–259, 1992 and K. E. Wagstaff, C. R. J. Woodhouse, P. G. Duffy, P. G. Ransley: Delayed linear growth in Children after enterocystoplasty. Br. J. Urol. 69; 314–317, 1992).

Disturbances to growth after bladder extension plasty during childhood and youth have been increasingly observed in recent years and are due both to the underlying disease and to the choice of the intestine segments used for augmentation.

Disturbances to ossary mineralisation after insertion of intestine into the bladder also occur in adults, even when kidney function is unimpaired (W. F. Whitemore and R. F. Gittes (1983), J. Urol, 129, 494–498). However patients who have not finished growing and have renal insufficiency are a group especially at risk.

One cause of this undoubtedly multi-level problem could be resorptive hyperchloraemic acidosis with subsequent injury in the bone system (M. O. Koch and W. S. McDougal (1985), Surgery 98, 561).

At present sodium bicarbonate for neutralisation is administered post-operatively to prevent the occurrence of acidosis and harmful consequences thereof during urine-bladder extension or replacement plasties. Since however acidosis occurs only in a fraction of patients after bladder extension or bladder replacement plasty, alkali therapy is an inadequate general method of avoiding the said after-effects of an operation. Furthermore, urine bladder extension or replacement plasties are a relatively new urine-evacuation process, with risks and mechanisms which have not yet been exhaustively researched.

SUMMARY OF THE INVENTION

The object of the invention is to propose effective treatment for preventing injury resulting from the use of a bladder extension or bladder replacement plasty, suitable both for adults and for children, for patients with or without renal insufficiency. It has unexpectedly been found that the after-effects on the bone system, which often take years to occur after an augmentation or replacement plasty, can be prevented or greatly reduced if the patient is given diphosphonic acids or physiologically compatible salts or esters thereof before, during and/or after the operation. Treatment can begin immediately after the operation or after administration of antibiotics has ceased.

The present invention provides methods for preventing disturbances to ossary mineralization in a patient after a urine bladder augmentation plasty or replacement plasty comprising administering to the patient having a urine bladder augmentation or replacement plasty at least one diphosphonic acid, physiologically compatible salt or ester thereof in an effective amount to reduce disturbances to ossary mineralization.

DETAILED DESCRIPTION OF THE INVENTION

According to the invention, at least one diphosphonic acid or physiologically compatible salt thereof is administered. Alternatively a number of diphosphonic acids or physiologically compatible salts thereof can be administered in combination.

The preferred group of diphosphonates for use are ibandronate, etidronate, clodronate, risedronate, pamidronate, zoledronate, incandronate, tiludronate, neridronate, olpadronate, EB-1053 ([1-hydroxy-3-(1-pyrrolindinyl)-propylidene]bis-phosphonate), YH 529 ([1-hydroxy-2-imidazo-(1,2-a)pyridin-3-yl ethylidene]bis-phosphonate) or alendronate. In principle, use can be made of other diphosphonic acids or physiologically compatible salts or physiologically compatible esters thereof.

Ibandronic acid (1-hydroxy-3-(N-methyl-N-pentyl) aminopropylidene-1,1-diphosphonic acid) or physiologically compatible salts thereof are particularly preferred.

Diphosphonic acids for treatment of calcium metabolism diseases are known. Drugs containing them are used for treatment of hypercalcaemia and also for treatment of tumor osteolysis resulting from bone metastases or for treatment of osteoporosis.

Use according to the invention immediately before, during and/or after urine-bladder augmentation or urine-bladder replacement for preventive treatment of disturbances in bone metabolism was not obvious to the operating urologist. The patients in question are a new group, treated preventively or therapeutically with diphosphonic acids.

Diphosphonates can be administered as liquids, solids, orally in aerosol form, enterally, parenterally, topically, transdermally, nasally, pulmonarily or rectally in all conventional non-toxic pharmaceutically acceptable excipients, adjuvants and additives. The term "parenteral" comprises subcutaneous, intravenous and intramuscular administration or infusions. Oral forms of application can e.g. be tablets, capsules, dragees, syrups, solutions, suspensions, emulsions, elixirs etc. containing one or more additives from the following groups, such as flavourings, sweeteners, dyes or preservatives. Oral forms of application containing the active constituent together with non-toxic pharmaceutically accepted excipients suitable for producing tablets, capsules, dragees etc. are e.g.: calcium carbonate, sodium carbonate, lactose, calcium phosphate or sodium phosphates; starch, mannitol, methyl cellulose, talcum, highly dispersed silicic acids, higher-molecular fatty acids such as stearic acid, peanut oil, olive oil, paraffin, miglyol, gelatine, agar agar, magnesium stearate, beeswax, cetyl alcohol, lecithin, glycerol, animal or vegetable fats, or solid high-molecular polymers such as polyethylene glycols. Tablets, capsules, dragees etc. can be given a suitable coating, e.g. of glyceryl monostearate or glyceryl distearate, to prevent undesired side-effects in the stomach, or to delay absorption in the gastro-intestinal tract and thus prolong the duration of action. The preferred injection media are sterile injectable aqueous or oily solutions or suspensions containing the usual additives such as stabilizers and solubilizers if required. Water, isotonic saline solution, 1,3-butanediol, fatty acids such as oleic acid, mono- and diglycerides or miglyol are examples of such additives. Rectal administration can be via any suitable non-irritant additives which are solid at normal temperature and liquid at rectal temperature, such as cocoa butter or polyethylene glycol. The usual pharmaceutical excipients can be used in aerosol form. Creams, tinctures, gels, solutions or suspensions etc. with the usual pharmaceutical additives are for external use.

Ibandronate of use as an injection solution according to the invention contains the active substance in a proportion of 0.05–2000 mg. The content of active substance for injection solutions of the other diphosphonates according to the invention will vary depending on their potency relative to ibandronate.

Depending on the clinical picture and medicinal aim (prevention and/or treatment), the diphosphonic acids can be applied daily or intermittently cyclically.

The daily i.v. equivalent dose is preferably 0.1 to 100 μg/kg ibandronate. The dosage of all other diphosphonics according to the invention will depend on their potency relative to ibandronate.

When other forms of application are used, the dosage must be adjusted in accordance with the bioavailability of the form of application.

The invention will now be explained with reference to exemplified embodiments.

EXAMPLES

Example 1

Preventive effect of diphosphonates before the occurrence of osteopenia after augmentation plasty. Groups of 12 female Sprague-Dawley rats (6–8 week old, about 80–100 kg body weight) were provided with stomach and ileum augmentation plasties and 12 animals were dummy-operated. At the same time, 24 animals were augmented with excluded sigma and divided at random into two groups, one group daily receiving a subcutaneous application of 0.9% NaCl (control) and the other group a daily subcutaneous application of ibandronic acid in the form of an aqueous solution in a dose up to 20 μg P/kg. The operative configuration of the augmentation plasties was after Lauvetz et al (J. Urol. 154: 899–902, 1995). The test period was 4 months, corresponding to about 4 years of human life (E. Grimm, Amer. J. Dig Dis. 7: 17–20, 1962).

Monthly radiological bone density measurements (DEXA) showed a statistically significant mineralisation deficit in the lumbar vertebrae of the ileum-augmented group (p<0.01) compared with the control group, and a tendency towards deficiency in the stomach and sigma group without ibandronate. In the sigma group treated with ibandronate there was no reduction in bone mass.

Example 2

To induce chronic kidney insufficiency (CNI), 24 rats were subjected to a 5/6 nephrectomy after Kleinknecht et al (Contr. Nephrol. 60: 27–38, 1988). Another group of 12 animals was dummy-operated.

a) The 12 dummy-operated animals were given 0.9% NaCl subcutaneously daily.
b) 12 animals with CNI were likewise given 0.9% NaCl subcutaneously daily.
c) Another 12 animals with CNI were daily given ibandronic acid in the form of an aqueous solution in a dose up to 20 μg P/kg.

The bone density measurement in the lumbar vertebrae by DEXA gave the following results:

| Group | a) NaCl | b) CNI + NaCl | c) CNI + ibandronate |
|---|---|---|---|
| Reduction in bone mass | ± | +++ | ± |

+ = Degree of reduction in bone mass compared with controls

Example 3

In order to increase the clinical relevance of the results, the test procedure of Example 2 was repeated on rats with chronic kidney insufficiency. This test arrangement is based on a frequent situation among human beings in which a bladder previously damaged by an existing disturbance in urine transport (reflux or obstruction) leads to kidney insufficiency as a secondary result. It is known that kidney insufficiency in itself results in a disturbance in bone mineralisation (renal osteopathy), so that the need for a bladder extension plasty using segments of intestine further increases the risk of disturbed mineralisation. Kidney insufficiency was induced by 5/6 nephrectomy (compare Example 2). The other test procedure was as in Example 1.

Result

It was found that the osteopenic effect of CNI was appreciably intensified by augmentation using the gastrointestinal segments. As before, a reduction in bone mass was prevented by administration of ibandronate.

What is claimed is:

1. A method for reducing the resulting side effects in patients who have had a urine bladder augmentation plasty or a replacement plasty through insertion of a segment of the intestine or stomach tissue comprising administering to said patient at least one diphosphonic acid, physiologically compatible salt or ester thereof in an effective amount to reduce the said resulting side effects.

2. The method of claim 1, wherein the diphosphonic acid, physiologically compatible salt or ester thereof is administered prior to the urine bladder augmentation or replacement plasty.

3. The method of claim 1, wherein the diphosphonic acid, physiologically compatible salt or ester thereof is administered during the urine bladder augmentation or replacement plasty.

4. The method of claim 1, wherein the diphosphonic acid, physiologically compatible salt or ester thereof is administered after the urine bladder augmentation or replacement plasty.

5. The method of claim 1, wherein the diphosphonic acid is selected from the group consisting of ibandronate, etidronate, clodronate, risedronate, pamidronate, zoledronate, incandronate, tiludronate, neridronate, olpadronate, EB-1053, YH 529, alendronate and physiologically compatible salts and esters thereof.

6. The method of claim 1, wherein the diphosphonic acid is ibandronate, said ibandronate being administered in an intravenous daily dosage amount of from about 0.1 µg/kg to about 100 µg/kg of body weight of said patient.

* * * * *